United States Patent [19]

Lagow et al.

[11] 4,110,474

[45] Aug. 29, 1978

[54] TETRAMETHYLPENTANE BLOOD SUBSTITUTES

[75] Inventors: Richard J. Lagow, Austin, Tex.; Lawrence A. Shimp, Hinsdale, Ill.; Leland C. Clark, Jr., Cincinnati, Ohio

[73] Assignees: Suntech, Inc., Philadelphia, Pa.; Children's Hospital Medical Center, Cincinnati, Ohio

[21] Appl. No.: 827,999

[22] Filed: Aug. 26, 1977

[51] Int. Cl.$^2$ ............................................. A61K 31/02
[52] U.S. Cl. .................................... 424/350; 260/653
[58] Field of Search ......................................... 424/350

[56] References Cited

U.S. PATENT DOCUMENTS

| | | | |
|---|---|---|---|
| 3,823,091 | 7/1974 | Samejima et al. | 424/350 |
| 3,989,843 | 11/1976 | Chabert et al. | 424/350 |

*Primary Examiner*—Sam Rosen
*Attorney, Agent, or Firm*—J. Edward Hess; Donald R. Johnson; Stanford M. Back

[57] ABSTRACT

Perfluorination of 2,2,4,4-tetramethylpentane by direct fluorination with $F_2$ or like reagents at low temperature, using inert gaseous diluents, yields a mixture of perfluoro 2,2,4,4-tetramethylpentane and 3-hydro-nonadecafluoro 2,2,4,4-tetramethylpentane together with lesser amounts of 3,3-dihydro-octadecafluoro 2,2,4,4-tetramethylpentane. The perfluoro and nonadecafluoro-tetramethylpentane mixture is useful in synthetic blood substitute compositions.

17 Claims, 1 Drawing Figure

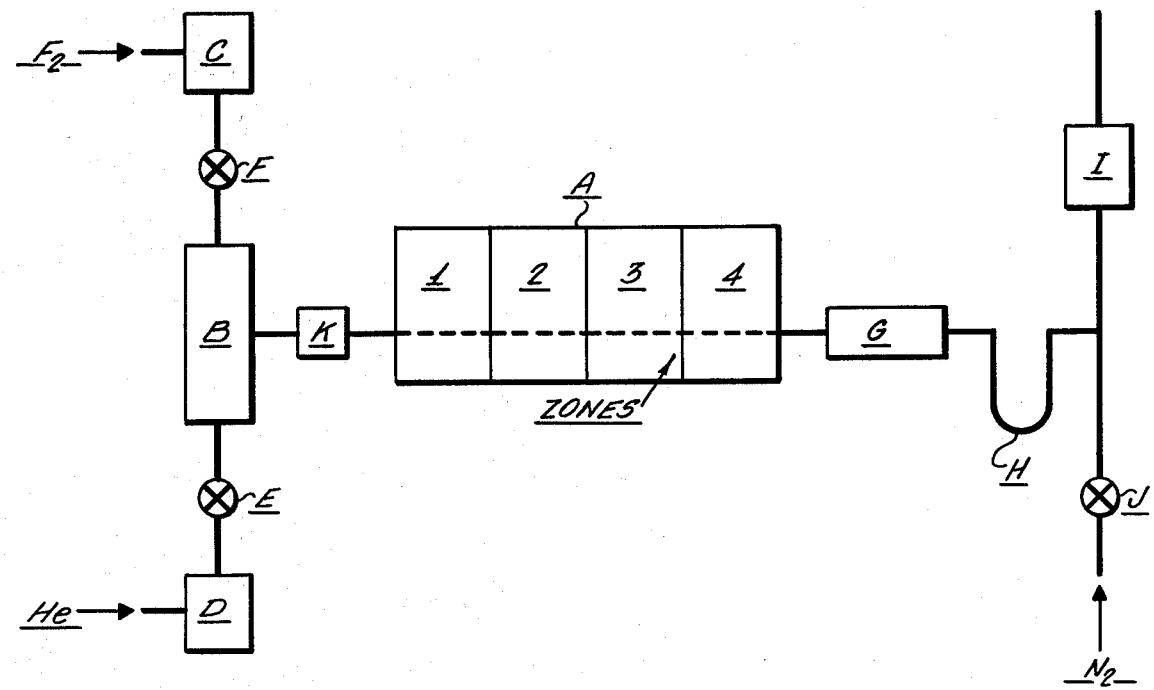

4,110,474

TETRAMETHYLPENTANE BLOOD SUBSTITUTES

BACKGROUND OF THE INVENTION

This invention relates to novel perfluorinated methylpentane compounds, and compositions containing the same which are useful as synthetic blood substitutes and/or perfusion media.

Clark, U.S. Pat. No. 3,911,138, issued Oct. 7, 1975, teaches that certain perfluorinated cyclic hydrocarbons, when emulsified, may be used as blood substitutes, i.e. as stable, readily available synthetic materials which are capable of carrying oxygen to and carbon dioxide from mammalian tissues when introduced into the blood stream. The cyclic materials of Clark perform this task effectively; however, the search continues for alternate materials which will serve equally well or better with respect to stability, toxicity, body retention time, and like properties.

SUMMARY OF THE INVENTION

In accordance with the present invention, there are provided novel fluorinated methylpenane compounds and compositions containing the same which are useful as synthetic blood substitutes and/or perfusion media. More particularly, this invention is directed to the direct fluorination of 2,2,4,4-tetramethylpentane to yield mixtures of the corresponding perfluoro 2,2,4,4-tetramethylpentane and 3-hydro-nonadecafluoro 2,2,4,4-tetramethylpentane. Together with smaller amounts of 3,3-dihydro-octadecafluoro 2,2,4,4-tetramethyl-pentane. This mixture, following the removal of the 3,3-dihydro compound, when emulsified with water and certain non-toxic emulsifying agents, provides a useful and highly effective synthetic blood substitute composition.

DESCRIPTION OF THE DRAWING

FIG. 1 is a diagrammatic drawing of a fluorination reactor fitted with mixing chambers and cooling traps as described in detail below.

DESCRIPTION OF THE INVENTION

Fluorination

The fluorination of 2,2,4,4-tetramethylpentane is readily accomplished by direct fluorination with $F_2$ gas under controlled reaction conditions. The reaction is preferably carried out in a multi-zoned reactor, desirably having four zones, to provide a temperature gradient across the reactor as the fluorine gas and tetramethylpentane are passed through it. The temperature gradient throughout the four zones of the reactor will vary depending upon the nature of the charge passing through. That is to say, as the charge containing the reactants is introduced into the first zone, that zone should desirably be maintained at about −80° to −75° C, while the other three zones are permitted to retain a general temperature of about 25° C. Thereafter, as the charge passes through the successive zones, each one of them in turn should be reduced to about −78° C while the others warm up to about 25° C. This regulation of the temperature in each zone is shown in further detail in the examples below.

It is essential that the fluorination be conducted in the presence of an inert gas such as helium, nitrogen or argon, of which helium is preferred. The fluorine should be mixed thoroughly with the inert gas before it is introduced into the reactor. Initially, the volume ratio of inert gas to fluorine should desirably be in the range of about 40 volumes of inert gas to about 3 volumes of fluorine. However, this ratio should gradually be reduced by reducing the amount of inert gas until finally essentially pure fluorine alone is being introduced into the reactor. This may conveniently be achieved by regulating the flow rate of the two gases into the reactor.

Finally, the weight ratio of fluorine to methylpentane should be about twice the stoichiometric amount so that nearly complete fluorine substitution will occur.

Alternate Fluorinating Agents

In a further embodiment of this invention $BrF_3$ or $ClF_3$ may be used in place of $F_2$ as the fluorinating agent, in which case there is obtained, in addition to the aforementioned fluorinated methylpentanes, small amounts of mixtures of brominated or chlorinated by-products of varying degrees of halogen substitution, including mixed halogenated brominated or chlorinated fluorine-substituted compounds. The exact composition of these mixtures is not precisely known. Their preparation, however, follows exactly the aforedescribed process using $F_2$ alone.

Apparatus

In the following examples, a typical reaction was carried out using a 4-zone reactor fitted with a mixing zone for the gases upstream from the reactor, and a cooling trap downstream from the outlet to trap the reaction product and unreacted methylpentane.

One typical reactor system is shown in FIG. 1. Part A is the main reactor. It consists of a nickel tube packed with copper turnings and passing through four traps (zones) that can be separately cooled. Part B is a mixing chamber in which metered amounts of fluorine and helium are mixed before entering the reactor. Part C is a Hastings model LF 50X flow meter used to measure the fluorine flow. Part D is a Matheson Gas model 600 flowmeter used to measure the helium flow. Parts E and F are metering valves. Part G is an NaF trap used to remove HF. Part H is a glass trap cooled by liquid nitrogen and used to trap volatile products. Part I is an $Al_2O_3$ trap used to remove unreacted fluorine. Valve J controls the nitrogen flow through trap I which is used to prevent oxygen from diffusing back into the reactor. Part K is a fitting that can be removed to allow material to be injected into the reactor.

Reaction Procedure

A typical reaction was started by first flushing the apparatus with 100 cc/min helium for 12 hours, then cooling zones one and two with a dry ice - isopropanol slush and injecting a measured amount of starting material through fitting K. The reaction was continued by cooling trap H with liquid nitrogen, adjusting the fluorine and helium flows to the desired rates, and filling and emptying the appropriate reactor zones. The reaction was ended by flushing with pure helium for 12 hours, then warming the reactor and letting the volatile products be carried into trap H by the helium flow. The conditions used for each reaction are shown in Table 1.

Product Characterization

The initial product separation was performed on a Bendix model 2300 gas chromatograph using a 25 foot, ⅜ inch diameter column packed with 10% SE-30 (a fluorosilicone) on Chromosorb P (an inert material) at 30°. 3,3-Dihydrooctadecafluoro-2,2,4,4-tetramethylpentane came off the column after 15 minutes, while the monohydro- and perfluoro- compounds came out together after 24 minutes. The latter two materials were then separated on a ten foot long, ¼ inch diameter column packed with 15% dinonylphthalate on Chromosorb P, at 10°. The perfluorocompound had a retention time of 10 minutes, while the monohydrocompound had a retention time of 12 minutes.

Table 1

Reaction Conditions

Reaction 1

| | | | |
|---|---|---|---|
| Starting material: 2,2,4,4-Tetramethylpentane, 1.6 g. | | | |
| Time (hr) | 16 | 24 | 36 |
| Zones cooled | 1,2 | 2,3 | 3,4 |
| $F_2$ flow (cc/min) | 1.5 | 1.5 | 1.5 |
| He flow (cc/min) | 20 | 8 | 0 |

Reaction 2

| | | | |
|---|---|---|---|
| Starting material: 2,2,4,4-Tetramethylpentane, 1.6g. | | | |
| Time (hr.) | 18 | 24 | 85 |
| Zones cooled | 1,2 | 2,3 | 3,4 |
| $F_2$ flow (cc/min) | 1.5 | 1.5 | 1.5 |
| He flow (cc/min) | 20 | 8 | 0 |

Reaction 3

| | | | |
|---|---|---|---|
| Starting material: 2,2,4,4-Tetramethylpentane, 0.8 g. | | | |
| Time (hr) | 18 | 24 | 80 |
| Zones cooled | 1,2 | 2,3 | 3,4 |
| $F_2$ flow (cc/min) | 1.5 | 1.5 | 1.5 |
| He flow (cc/min) | 20 | 8 | 0 |

Reaction 4

| | | |
|---|---|---|
| Starting material: 3,3-dihydrooctadecafluoro-2,2,4,4-tetramethylpentane, 0.5 g. | | |
| Time (hr) | 24 | 48 |
| Zones cooled | 2,3 | 3,4 |
| $F_2$ flow (cc/min) | 1.5 | 1.5 |
| He flow (cc/min) | 0 | 0 |

PRODUCTS: CHARACTERIZING DATA 3,3-Dihydrooctadecafluoro-2,2,4,4-tetramethylpentane Anal. C,23.89% H, 0.44%; F, 75.66%. Found: C, 23.69%; H, 0.39%, F, 75.64%. The $^{19}$F NMR consisted of a singlet at −11.7 ppm from an external trifluoroacetic acid reference. The $^1$H NMR consisted of a singlet at 7.18τ. The gas phase infrared spectrum contained bands at (cm$^{-1}$) 3025(w), 1460(w), 1315(s), 1295(vs), 1260(s), 1215(w), 1185(m), 1095(m), 1045(s), 990(m), 740(m), 695(m). The mass spectrum at 70 e.V contained a parent minus fluorine peat at m/e 433. The melting point was between −38° and −39°.

3-Hydro-nonadecafluoro-2,2,4,4-tetramethylpentane

Anal. C, 22.98%; H, 0.21%; F, 76.81%. Found: C, 22.93%; H, 0.18%; F, 76.72%. The $^{19}$F NMR consisted of a doublet (from the $CF_3$ groups) centered at −13.8 ppm from an external trifluoroacetic acid reference. The $^1$H NMR spectrum consisted of a doublet centered at 4.34τ. The coupling constant, $J_{FH}$, was 36.6 Hz. The gas phase infrared spectrum contained bands at (cm$^{-1}$) 1440(w), 1365(m), 1300(vs), 1290(vs), 1265(s), 1225(w), 1195(m), 1165(w), 1080(w), 1045(s), 995(s), 975(w), 795(w), 775(m), 745(m), 715(m). The mass spectrum at 70 e.V. contained no peaks above m/e 381 ($C_8F_{15}^+$). The melting point was between −33° and −34° C.

Perfluoro-2,2,4,4-tetramethylpentane

Anal. C, 22.13%; F, 77.87%. Found: C, 22.58%; F, 77.63%. The F NMR spectrum consisted of a triplet (from the $CF_3$ groups) centered at −17.1 ppm from an external trifluoroacetic acid reference. The coupling constant, $J_{FF}$, was 14.9 Hz. The signal from the two fluorines on the center carbon atom would be expected to a 19 line multiplet, but was of too low intensity to be observed. The gas phase infrared spectrum contained bands at (cm$^{-1}$) 1300(vs), 1285(vs), 1270(s), 1235(w), 1195(s), 1175(w), 1150(w), 1095(w), 1025(w), 990(s), 815(m), 750(m), 740(s), 715(m). The mass spectrum at 70 e.V. contained a parent minus fluorine peak at m/e 469. The melting point was between −24° and −25°.

Results

The first run, which lasted for 76 hours, resulted in the formation of the perfluoro-, monohydro- and dihydrotetramethylpentane compounds in ratios of about 0.20 to 0.66 to 0.14 (as determined by integration of the NMR spectrum of the raw product mixture), with a total yield of about 70%. The second reaction, run under the same conditions except that the time interval with pure fluorine was increased from 36 hours to 85 hours, gave the same ratios of the perfluoro-, monohydro- and dihydro- products, but the total yield was increased to about 95%. The third run, which was identical to the second except that half the amount of starting material was used, gave the same results as the second run. The fourth run, an attempted fluorination of the pure dihydro- compound, resulted in no change in the starting material.

Synthetic Blood: Emulsification and Test Results

A synthetic blood must have several characteristics. Initially, and quite obviously, it must have high oxygen and carbon dioxide solubility since its principal function is to transport oxygen and carbon dioxide. A synthetic blood also must be non-toxic and in this respect it is desirable that when the synthetic blood is replaced by natural blood there is no residue of the former left in vital body organs.

Another characteristic of blood substitutes is that they must have certain vapor pressure requirements. The blood substitutes leave the body by being exhaled and by vaporization through the skin. Preferably the substitute leaves the body at about the same rate that new natural blood is being generated by the body. If the vapor pressure of the substitute is too low it stays in the body too long, whereas if it is too high it creates problems akin to the "bends".

Blood substitutes must also be capable of forming very stable emulsions with this capability being even more important with perfusion materials. Fluorocarbons are usually immiscible with blood and if used alone could cause embolisms. This problem is overcome by using it in an aqueous emulsion and obviously the emulsion should not separate in use or storage. In connection with perfusion materials this stability is even more strict because the oxygenators used to add oxygen to the perfusion material create very high shear and will break down all but the most stable emulsions. Another reason aqueous emulsions are employed is that salts are added to the water in order to maintain the body salt balance.

Emulsification

The perfluorinated methylpentanes are employed as a water emulsion, desirably containing more than 40% water by volume. Preferably the emulsion contains 10–30 volume percent of about a 50:50 mixture comprising perfluoro 2,2,4,4-tetramethylpentane and 3-hydrononadecafluoro 2,2,4,4-tetramethylpentane, although either of these materials alone may also be used. Normally the emulsion will contain 1-5 volume percent of an emulsifier. The specific emulsifier employed is not critical but it should itself be nontoxic and should form a stable emulsion. The preferred emulsifier is a yolk-phospholipid as this is well known to be harmless in the body. Also suitable for perfusion purposes are the polyoxyethylenes and polyoxypropylenes available commercially as "pluronics". "Pluronic F-68" has a molecular weight of 8350 and forms a very stable emulsion. However there is some unconfirmed reports that "Pluronic" type materials precipitate plasma protein and hence they are preferably limited to perfusion, with the commercially available yolk-phospholipids used for blood substitutes.

The emulsion can be formd with conventional high shear emulsifiers such as the Manton-Gaulin homogenizer. Typically, the particle size of the perfluoropolycyclic in the emulsion is 0.001-10 microns, frequently 0.01-10 micron, usually 0.05-0.5 micron and preferably 50 weight percent of the particles have diameters of 0.05-0.3 micron. As is well known the particle size can be adjusted by the amount of shear employed. The smaller particle size is preferred since it has been found that the resulting emulsions are more stable as particle size is reduced.

In the following test results, by "perfluoromethylpentane" is meant an approximately 50:50 mixture of the perfluoro compound and its monohydro-counterpart.

Test Results: Liver and Spleen Retention

The perfluoromethylpentanes lack body retention characteristics, as shown below.

Emulsions containing 10% of the material to be tested, surfactant and water were made up and tested in the manner specified in Science, Vol. 181, August 1973, page 681. Mice were injected with the various emulsions. The mice were killed at intervals thereafter, the liver and spleen analyzed, and the percentage of original amount of PF material injected and still in the liver and spleen was determined. The data below show these results.

| TIME FROM INFUS. | DOSE (ml/kg) | % FC (Of Injected Dose) | |
|---|---|---|---|
| | | LIVER | SPLEEN |
| 2 days | 150 | 15 | 1.4 |
| 7 days | 75 | 12 | 6 |
| 14 days | 75 | 9.3% | 9.2% |
| 29 days | 100 | 2.3 | 2.7 |

Test Results: $LD_{50}$

It has also been found that the perfluormethylpentanes are very nontoxic. The $LD_{50}$ after infusion (ml/kg) of these materials is shown below.

The material consisted of a 10% emulsion of the perfluoromethylpentane containing a %5 F-68 surfactant.

| DOSE cc/kg | N | 10Min. | 1Hours | 1Day | 2D | 3D | 4D | 5D | 6D | 7D |
|---|---|---|---|---|---|---|---|---|---|---|
| 150 | 1 | 1 | 1 | 1 | 0 | 0 | 0 | 0 | 0 | 0 |
| 100 | 1 | 1 | 1 | 1 | 1 | 1 | 1 | 1 | 1 | 1 |
| 75 | 2 | 2 | 2 | 2 | 2 | 2 | 2 | 2 | 2 | 2 |
| Total | 4 | 4 | 4 | 4 | 3 | 3 | 3 | 3 | 3 | 3 |
| MEAN | | | | | | | | | | |
| S.D. | | | | | | | | | | |
| $LD_{50}$ | >150 | >150 | >150 | >150 | ~110 | ~110 | ~110 | ~110 | ~110 | ~110 |

The perfluorinated materials of the invention have high oxygen and carbon dioxide solubility. For example the perfluorinated materials when oxygenated contain as much as about 40-60 cc oxygen per 100 cc fluorocarbon and the carbon dioxide solubility is about twice this. Normally blood will absorb about 20 cc oxygen per 100 cc of blood with carbon dioxide solubility being twice that of oxygen. The compositions of our invention will normally contain 30-60 cc of oxygen per 100 cc of the perfluorinated material but ratios as low as 10 cc per 100 cc can be used, and higher amounts such as 100 cc per 100 cc can be used where available. All the foregoing solubilities are at 25° C and 760 milliliters mercury.

The invention claimed is:

1. An artificial blood comprising an emulsion of a mixture comprising perfluoro 2,2,4,4-tetramethylpentane and 3-hydro-nonadecafluro 2,2,4,4-tetramethylpentane in water, said emulsion containing a non-toxic emulsifier.

2. The composition according to claim 1 wherein the amount of said fluorinated mixture is 10-30% by volume of the total emulsion.

3. The composition according to claim 1 which additionally contains 10-100 cc $O_2$ (25° C, 760 mm Hg) per 100 cc of said fluorinated mixture.

4. Composition according to claim 1 wherein the particle size of the fluorinated materials in the emulsion is from about 0.001 to 10 microns.

5. The composition according to claim 4 wherein about 50 weight percent of the particles have diameters of from about 0.05 to 0.3 microns.

6. The composition according to claim 1 wherein the amount of water is greater than 40% by volume.

7. A method for supporting oxygen-carbon dioxide transport in an animal body which comprises intravascular administration of an artificial blood defined in claim 1.

8. A method for supporting oxygen transfer in an animal organ which comprises externally perfusing the animal organ with an artificial blood defined in claim 1 having oxygen dissolved therein, the perfluorinated material in said blood having a vapor pressure which permits it to leave the organ without causing adverse gas collection in the organ tissue.

9. An artificial blood comprising an emulsion of a fluorinated material in water, said emulsion containing a nontoxic emulsifier and said fluorinated material being obtained by fluroination of 2,2,4,4-tetramethylpentane with $BrF_3$ in an inert gaseous diluent at elevated temperatures.

10. The composition according to claim 9 wherein the amount of said fluorinated mixture is 10-30% of the total emulsion.

11. The composition according to claim 9 which additionally contains 10–100 cc $O_2$ (25° C, 760 mm Hg) per 100 cc of said fluorinated mixture.

12. The composition according to claim 9 wherein the particle size of the fluorinated materials in the emulsion is from about 0.001 to 10 microns.

13. The composition according to claim 9 wherein about 50 weight percent of the particles have diameters of from about 0.05 to 0.3 microns.

14. The composition according to claim 9 wherein the amount of water is greater than 40% by volume.

15. A method for supporting oxygen-carbon dioxide transport in an animal body which comprises intravascular administration of an artificial blood defined in claim 9.

16. A method for supporting oxygen transfer in an animal organ which comprises externally perfusing the animal organ with an artificial blood defined in claim 9 having oxygen dissolved therein, the perfluorinated material in said blood having a vapor pressure which permits it to leave the organ without causing adverse gas collection in the organ tissue.

17. A mixture comprising perfluoro-2,2,4,4-tetramethylpentane and 3-hydro-nonadecafluro-2,2,4,4-tetramethylpentane.

* * * * *